United States Patent [19]
MacLean et al.

[11] Patent Number: 5,889,042
[45] Date of Patent: Mar. 30, 1999

[54] METHOD OF TREATING DISEASES AND CONDITIONS WITH ESTROGEN AGONISTS AND ANTAGONISTS

[75] Inventors: David B. MacLean, Providence, R.I.; David D. Thompson, Gales Ferry, Conn.

[73] Assignee: Pfizer Inc., New York, N.Y.

[21] Appl. No.: 803,706

[22] Filed: Feb. 21, 1997

Related U.S. Application Data

[60] Provisional application No. 60/013,213, Feb. 28, 1996.

[51] Int. Cl.$^6$ .................................................. A61K 31/40
[52] U.S. Cl. ............................................................ 514/127
[58] Field of Search ............................................ 514/427

[56] References Cited

U.S. PATENT DOCUMENTS

| | | | |
|---|---|---|---|
| 4,418,068 | 11/1983 | Jones | 424/267 |
| 4,859,585 | 8/1989 | Sonnenschein | 435/29 |
| 5,047,431 | 9/1991 | Schickaneder et al. | 514/648 |
| 5,254,594 | 10/1993 | Kazuaki et al. | 514/648 |
| 5,364,791 | 11/1994 | Vegeto et al. | 435/320.1 |
| 5,384,332 | 1/1995 | Fontana | 514/648 |
| 5,389,670 | 2/1995 | Fontana | 514/443 |
| 5,391,557 | 2/1995 | Cullinan et al. | 514/324 |
| 5,393,763 | 2/1995 | Black et al. | 514/333 |
| 5,418,252 | 5/1995 | Williams | 514/443 |
| 5,434,166 | 7/1995 | Glasebrook | 514/317 |
| 5,439,923 | 8/1995 | Cullinan | 514/324 |
| 5,439,931 | 8/1995 | Sales | 514/443 |
| 5,441,966 | 8/1995 | Dodge | 514/324 |
| 5,441,986 | 8/1995 | Thompson | 514/648 |
| 5,446,053 | 8/1995 | Koehane | 514/324 |
| 5,447,941 | 9/1995 | Zuckerman | 514/324 |
| 5,451,589 | 9/1995 | Dodge | 514/324 |
| 5,451,590 | 9/1995 | Dodge | 514/324 |
| 5,455,275 | 10/1995 | Fontana | 514/648 |
| 5,457,113 | 10/1995 | Cullinan | 514/319 |
| 5,457,116 | 10/1995 | Black et al. | 514/324 |
| 5,457,117 | 10/1995 | Black et al. | 514/337 |
| 5,461,064 | 10/1995 | Cullinan | 514/324 |
| 5,461,065 | 10/1995 | Black et al. | 514/324 |
| 5,462,937 | 10/1995 | Cullinan et al. | 514/212 |
| 5,462,949 | 10/1995 | Jones et al. | 514/324 |
| 5,462,950 | 10/1995 | Fontana | 514/324 |
| 5,464,845 | 11/1995 | Black et al. | 514/326 |
| 5,470,883 | 11/1995 | Stromberg | 514/648 |
| 5,550,164 | 8/1996 | Fontana | 514/648 |

FOREIGN PATENT DOCUMENTS

| | | | |
|---|---|---|---|
| 0309473 | 5/1991 | European Pat. Off. | A61L 33/00 |
| 0659415 | 12/1994 | European Pat. Off. | A61K 31/445 |
| 0659429 | 12/1994 | European Pat. Off. | A61K 31/445 |
| 0664126 | 12/1994 | European Pat. Off. | A61K 31/445 |
| 0635264 | 1/1995 | European Pat. Off. | A61K 31/135 |
| 0659413 | 6/1995 | European Pat. Off. | A61K 31/445 |
| 0659414 | 6/1995 | European Pat. Off. | A61K 31/445 |
| 0659418 | 6/1995 | European Pat. Off. | A61K 31/445 |
| 0659419 | 6/1995 | European Pat. Off. | A61K 31/445 |
| 0659424 | 6/1995 | European Pat. Off. | A61K 31/445 |
| 0659425 | 6/1995 | European Pat. Off. | A61K 31/445 |
| 0659427 | 6/1995 | European Pat. Off. | A61K 31/445 |
| 0659428 | 6/1995 | European Pat. Off. | A61K 31/445 |
| 0664121 | 7/1995 | European Pat. Off. | A61K 31/445 |
| 0664123 | 7/1995 | European Pat. Off. | A61K 31/445 |
| 0664125 | 7/1995 | European Pat. Off. | A61K 31/445 |
| 0652004 | 10/1995 | European Pat. Off. | A61K 31/445 |

OTHER PUBLICATIONS

Klaus, S. et al. "In Vivo and in Vitro Antiestrogenic Action of 3–Hydroxytamoxifen, Tamoxifen and 4–Hydroxytamoxifen," *Eur. J. Clin. Oncol.*, vol. 21, No. 8, pp. 985–990, 1985.

Eppenberger, U. et al. "Pharmacologic and Biologic Properties of Droloxifene, A New Antiestrogen," *Am. J. Clin. Oncol (CCT)* 14, Suppl. 2, pp. S5–S14, 1991.

*Primary Examiner*—Jerome D. Goldberg
*Attorney, Agent, or Firm*—Peter C. Richardson; Paul H. Ginsburg; Garth Butterfield

[57] ABSTRACT

Compounds of this formula

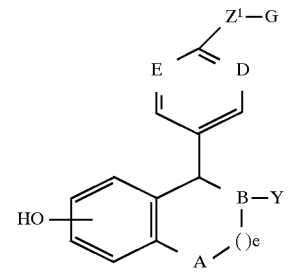

are useful for treating or preventing Alzheimer's disease, premenstrual syndrome, peri-menopausal syndrome, a deficiency of thrombomodulin, uterine fibrosis, excessive myeloproxidase activity, excessive thrombin, autoimmune disease, reperfusion damage of ischemic myocardium and insufficient testosterone.

1 Claim, No Drawings

METHOD OF TREATING DISEASES AND CONDITIONS WITH ESTROGEN AGONISTS AND ANTAGONISTS

This is a continuation of provisional application Ser. No. 60/013,213 filed Feb. 28, 1996, the benefit of which is hereby claimed under 37 C.F.R. §1.78(a)(3).

BACKGROUND OF THE INVENTION

Certain estrogen agonists have been reported to be useful in inhibiting pathological conditions related to organ systems which respond to estrogen agonists or antagonists. In particular, 2-phenyl-3-aroylbenzothiophenes and 1-(alkylaminoethoxy phenyl)-1-phenyl-2-phenylbut-1-enes represented by raloxifene and tamoxifen have wide application as estrogen agonists.

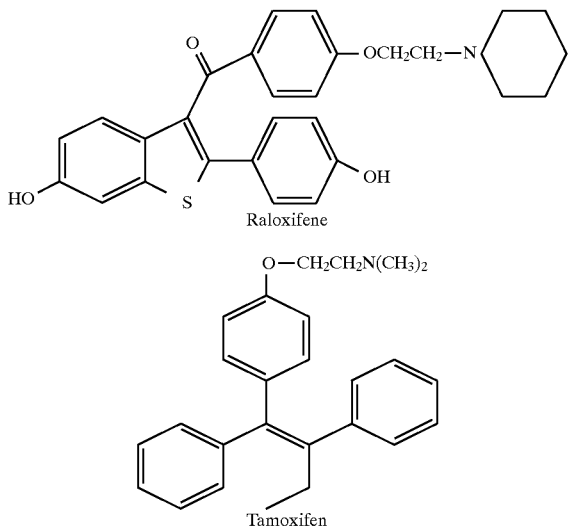

Raloxifene has been claimed to be effective in the treatment of acne, U.S. Pat. No. 5,439,923; alopecia, EP 0659414 A2; Alzheimers disease, EP 0659418 A1; atrophy of skin and vagina, U.S. Pat. No. 5,461,064; auto immune disease, EP 0664123; breast cancer, U.S. Pat. No. 4,418,068; breast disease, EP 0659419; cartilage degeneration, U.S. Pat. No. 5,418,252; CNS problems (post menopausal), 94 EP 0309470; pathology of endocrine target organs, U.S. Pat. No. 4,418,068; delayed puberty, U.S. Pat. No. 5,451,589; demyelinating disease, U.S. Pat. No. 5,434,166; dysmyelinating disease, U.S. Pat. No. 5,434,166; dysmenorrhea, U.S. Pat. No. 5,446,053; endometriosis, U.S. Pat. No. 5,461,065; female infertility, EP 659429 A1; fertility disorders; hirsutism, EP 0659414 A2; hypoglycemic, EP 635264 A2; increase libido, U.S. Pat. No. 5,439,931; inhibition of fertility, U.S. Pat. No. 5,462,949; LDL oxidation, EP 0664121 A; hypercholesterolemia, U.S. Pat. No. 5,464,845; lupus erythematosus, EP 0664125; impaired macrophage function, EP 659425 A1; male infertility, EP 0659424 A1; myocardial infaction, ischaemia, thromboembolic disorder, thrombin inhibition, EP 0664126; menopausal disorders, EP 0659415; menstruation disorders, U.S. Pat. No. 5,462,950; obesity, 94 EP 0309481; obsessive compulsive disorder, EP 0659428; osteoporosis, U.S. Pat. No. 5,457,117; ovarian dysgenesis, US 5,451,589; peri-menopausal syndrome, U.S. Pat. No. 5,391,557; peripheral vasoconstriction, U.S. Pat. No. 5,470,883; post menopausal CNS, EP 0659415; pre-menstrual syndrome, U.S. Pat. No. 5,389,670; prostatic carcinoma; prostatic hyperplasia; pulmonary hypertension, U.S. Pat. No. 5,447,941; reperfusion damage, J. AM. Cardiol 25, 189A (1993); resistant neoplasm, EP 0652004 A1; restenosis, U.S. Pat. No. 5,462,937; rheumatoid arthritis, EP 0664125; seborrhea, U.S. Pat. No. 5,439,923; sexual dysfunction; sexual precocity, U.S. Pat. No. 5,451,590; thrombomodulin expression, EP 0659427; Turners syndrome, U.S. Pat. No. 5,441,966; uterine fibrosis U.S. Pat. No. 5,457,116; and vasomotor symptoms (post menopausal), 94 EP 0309473.

Tamoxifen is widely employed in the treatment of breast cancer and has been reported to be effective in the treatment of the following diseases and conditions: high lipid levels, Drug Ther. 22/3, 109 (1992); ovarian cancer, J. Clin. Oncol. 11, No. 10, 1957–68 (1993); renal cell carcinoma, Br. J. Radiol 56, No. 670, 766–7 (1983); suppression of atherogenic factor homocysteine, Env. J. Cancer 29 Suppl. 6, S110 (1993); metastatic melanoma, J. Clin. Oncol. 12, No. 8, 1553–60 (1994); mastalgia, Drugs 32, No. 6, 477–80, (1986); prolactive secreting pituitary tumors, J. Endrocrinol. Invest. 3/4, 343–347 (1980); osteoporosis, Proc. Annu Meet Am Assoc. Cancer Res.; 33: A566-7 (1992); netroperitoneal fibrosis, Lancet 341, No. 8841, 382 (1993).

Small structural changes in the structure of estrogen agonists cause profound differences in biological properties. For example, droloxifene (3-hydroxytamoxifen) formula I below, has a 10-60-fold higher binding affinity to the estrogen receptor compared to tamoxifen. Droloxifene is devoid of in vivo or in vitro carcinogenic or mutagenic effects, whereas tamoxifen causes liver tumors in rats. Hasmamu, et al. Cancer Letter 84, 101–116 (1994).

Droloxifene has been reported to be effective in the treatment of breast cancer U.S. Pat. No. 5,047,431; endometriosis, U.S. Pat. No. 5,455,275; lowering cholesterol, U.S. Pat. No. 5,426,123; osteoporosis, U.S. Pat. No. 5,254,594; prostatic hyperplasia, U.S. Pat. No. 5,441,986; and restenosis, U.S. Pat. No. 5,384,332.

SUMMARY OF THE INVENTION

This invention provides a method of inhibiting a pathological condition selected from the group consisting of Alzheimer's disease, premenstrual syndrome, peri-menopausal syndrome, a deficiency of thrombomodulin, uterine fibrosis, excessive myeloperoxidase activity, excessive thrombin, autoimmune disease, reperfusion damage of ischemic myocardium and insufficient testosterone which comprises administering to a mammal in need of said pathological condition an effective amount of a compound of the formula

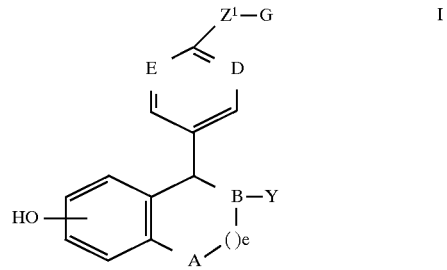

wherein:
A is selected from $CH_2$ and NR;
B, D and E are independently selected from CH and N;
Y is
(a) phenyl, optionally substituted with 1–3 substituents independently selected from $R^4$;

(b) naphthyl, optionally substituted with 1–3 substituents independently selected from $R^4$;
(c) $C_3$–$C_8$ cycloalkyl, optionally substituted with 1–2 substituents independently selected from $R^4$;
(d) $C_3$–$C_8$ cycloalkenyl, optionally substituted with 1–2 substituents independently selected from $R^4$;
(e) a five membered heterocycle containing up to two heteroatoms selected from the group consisting of —O—, —$NR^2$— and —$S(O)_n$—, optionally substituted with 1–3 substituents independently selected from $R^4$;
(f) a six membered heterocycle containing up to two heteroatoms selected from the group consisting of —O—, —$NR^2$— and —$S(O)_n$— optionally substituted with 1–3 substituents independently selected from $R^4$; or
(g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from $R^4$;

$Z^1$ is
(a) —$(CH_2)_p$ $W(CH_2)_q$—;
(b) —$O(CH_2)_p$ $CR^5R^6$—;
(c) —$O(CH_2)_p W(CH_2)_q$;
(d) —$OCHR^2CHR^3$—; or
(e) —$SCHR^2CHR^3$—;

G is
(a) —$NR^7R^8$;
(b)

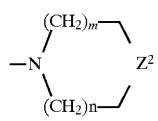

wherein n is 0, 1 or 2; m is 1, 2 or 3; $Z^2$ is —NH—, —O—, —S—, or —$CH_2$—; optionally fused on adjacent carbon atoms with one or two phenyl rings and, optionally independently substituted on carbon with one to three substituents and, optionally, independently on nitrogen with a chemically suitable substituent selected from $R^4$; or (c) a bicyclic amine containing five to twelve carbon atoms, either bridged or fused and optionally substituted with 1–3 substituents independently selected from $R^4$; or $Z^1$ and G in combination may be

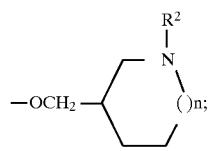

W is
(a) —$CH_2$—;
(b) —CH=CH—;
(c) —O—;
(d) —$NR^2$—;
(e) —$S(O)_n$—;

(f)

(g) —$CR^2(OH)$—;
(h) —$CONR^2$—;
(i) —$NR^2CO$—;
(j)

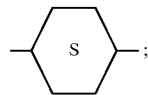

or
(k) —C≡C—;

R is hydrogen or $C_1$–$C_6$ alkyl;
$R^2$ and $R^3$ are independently
(a) hydrogen; or
(b) $C_1$–$C_4$ alkyl;
$R^4$ is
(a) hydrogen;
(b) halogen;
(c) $C_1$–$C_6$ alkyl;
(d) $C_1$–$C_4$ alkoxy;
(e) $C_1$–$C_4$ acyloxy;
(f) $C_1$–$C_4$ alkylthio;
(g) $C_1$–$C_4$ alkylsulfinyl;
(h) $C_1$–$C_4$ alkylsulfonyl;
(i) hydroxy ($C_1$–$C_4$)alkyl;
(j) aryl ($C_1$–$C_4$)alkyl;
(k) —$CO_2H$;
(l) —CN;
(m) —CONHOR;
(n) —$SO_2NHR$;
(o) —$NH_2$;
(p) $C_1$–$C_4$ alkylamino;
(q) $C_1$–$C_4$ dialkylamino;
(r) —$NHSO_2R$;
(s) —$NO_2$;
(t) —aryl; or
(u) —OH.

$R^5$ and $R^6$ are independently $C_1$–$C_8$ alkyl or together form a $C_3$–$C_{10}$ carbocyclic ring;
$R^7$ and $R^8$ are independently
(a) phenyl;
(b) a $C_3$–$C_{10}$ carbocyclic ring, saturated or unsaturated;
(C) a $C_3$–$C_{10}$ heterocyclic ring containing up to two heteroatoms, selected from —O—, —N— and —S—;
(d) H;
(e) $C_1$–$C_6$ alkyl; or
(f) form a 3 to 8 membered nitrogen containing ring with $R^5$ or $R^6$; $R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;
e is 0, 1 or 2;
m is 1, 2 or 3;
n is 0, 1 or 2;
p is 0, 1, 2 or 3;
q is 0, 1, 2 or 3;

and optical and geometric isomers thereof; and nontoxic pharmacologically acceptable acid addition salts, N-oxides, and quaternary ammonium salts thereof.

Preferred compounds of formula I are of the formula:

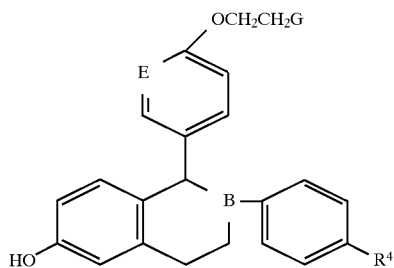

wherein G is

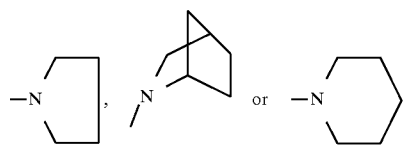

; and

R⁴ is H, OH, F, or Cl; and B and E are independently selected from CH and N.

Especially preferred compounds are:

Cis-6-(4-fluoro-phenyl)-5-[4-(2-piperidin-1-yl-ethoxy)-phenyl]-5,6,7,8-tetrahydro-naphthalen-2-ol;

(−)-Cis-6-phenyl-5-[4-(2-pyrrolidin-1-yl-ethoxy)-phenyl]-5,6,7,8-tetrahydro-naphthalen-2-ol;

Cis-6-phenyl-5-[4-(2-pyrrolidin-1-yl-ethoxy)-phenyl]5,6,7,8-tetrahydro-naphthalen-2-ol;

Cis-1-[6'-pyrrolodinoethoxy-3'-pyridyl]-2-phenyl-6-hydroxy-1,2,3,4-tetrahydrohaphthalene;

1-(4'-Pyrrolidinoethoxyphenyl)-2-(4"-fluorophenyl)-6-hydroxy-1,2,3,4-tetrahydroisoquinoline;

Cis6(4-hydroxyphenyl)-5-[4-(2-piperidin-1-yl-ethoxy)-phenyl]-5,6,7,8-tetrahydro-naphthalen-2-ol; and 1-(4'-Pyrrolidinolethoxyphenyl)-2-phenyl-6-hydroxy-1,2,3,4-tetrahydroisoquinoline.

DETAILED DESCRIPTION OF THE INVENTION

The present invention provides methods for inhibiting pathological conditions which are susceptible or partially susceptible to inhibition by an estrogen, antiestrogen or estrogen agonist. Such conditions include Alzheimer's disease, premenstrual syndrome, peri-menopausal syndrome, a deficiency of thrombomodulin, uterine fibrosis, excessive myeloproxidase activity, excessive thrombin, autoimmune disease, reperfusion damage of ischemic myocardium and insufficient testosterone.

Alzheimer's Disease (AD) is a degenerative brain disorder characterized clinically by progressive loss of memory, cognition, reasoning, judgment and emotional stability that gradually leads to profound mental deterioration and ultimately death. AD is a common cause of progressive mental failure (dementia) in aged humans and is believed to represent the fourth most common medical cause of death in the United States. AD has been observed in varied races and ethnic groups worldwide and presents a major present and future public health problem. The disease is currently estimated to affect about two to three million individuals in the United States alone. To date, AD has proven to be incurable.

The brains of individuals with AD exhibit neuronal degeneration and characteristic lesions variously referred to as amyloidogenic plaques, vascular amyloid angiopathy, and neurofibrillary tangles. Large numbers of these lesions, particularly amyloidogenic plaques and neurofibrillary tangles, are generally found in several areas of the human brain important for memory and cognitive function in patients with AD. Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

Several lines of evidence indicate that progressive cerebral deposition of particular amyloidogenic proteins, β-amyloid proteins, (βAP), play a seminal role in the pathogenesis of AD and can precede cognitive symptoms by years or decades. See, Selkoe, (1991) Neuron 6:487. Recently, it has been shown that βAP is released from neuronal cells grown in culture and is present in cerebrospinal fluid (CSF) of both normal individuals and AD patients. See, Seubert et al., (1992) Nature 359:325–327.

A possible correlation to the plaque pathology has been developed by several groups demonstrating the direct βAP neurotoxicity toward, cultured neurons. Direct neurotoxicity of βAP was recently reported to be attenuated by co-treatment with TGF-β (Chao et al., Soc. Neurosci. Abs., 19:1251 (1993)).

More recently, in addition to the direct neurotoxicity, an inflammatory response in the AD brain, perhaps elicited by βAP, also contributes to the pathology of the disease. A limited clinical trial with the NSAID indomethacin exhibited a retardation in the progression of Alzheimer's dementia (Rogers et al., Science, 260:1719–1720 (1993)). European Patent Application 0659418 A1 describes the use of certain benzothiophenenes for the inhibition of Alzheimer's Disease.

Despite the progress that has been made in understanding the underlying mechanisms of AD, there remains a need to develop compositions and methods for treatment of these diseases. Treatment methods could advantageously be based on drugs which are capable of increasing TGF-β expression in the brain, thus ameliorating the β-amyloid peptide mediated neurotoxicity and inflammatory response associated with AD.

Each month, for a few days prior to the onset of menstruation, many millions of otherwise-healthy women develop symptoms of disturbed mood and appetite that can be strikingly similar to those reported by patients with Seasonal Affective Disorder (SAD), carbohydrate-craving obesity, or the non-anorexic variants of bulimia. This syndrome was first termed "premenstrual tension" by R. T. Frank in 1931 and is a very common phenomenon. According to Guy Abraham of UCLA, of every ten patients to walk into a gynecologists office, three or four will suffer from premenstrual tension and, in some, the symptoms will be of such severity as to include attempts at suicide. Current Progress in Obstetrics and Gynecology, 3:5–39 (1980).

Initial descriptions of the Premenstrual Syndrome (PMS) focused on its association with nervous tension, headache, and weight gain. The weight gain observed was initially attributed to excessive retention of salt and water, which does indeed occur in some PMS patients. However, it soon became evident that it was also a consequence of the widespread tendency of individuals suffering from PMS to crave and overconsume carbohydrates, particularly foods with a sweet taste. PMS is also now referred to as late luteal phase syndrome (or late luteal phase dysphoric disorder). D.N.S. III, Revised, American Psychiatric Association (1987).

There have been numerous suggestions made about the etiology of PMS. For example, some hypothesized that it was caused by a uterine toxin. Others suggested its cause was overconsumption of sweets, which was presumably followed by excessive insulin secretion, hypoglycemia, and inadequate brain glucose, and resulted in the often observed depression and anxiety. It also has been postulated that the behavioral symptoms result from the tissue edema often observed and that the psychological changes result from feelings of loss or the social complexities generated by the discomforts of menstruation.

However, none of these theories has been substantiated: PMS can persist after hysterectomy and, hence, uterine toxins cannot be its cause; the hyperinsulinism of PMS is not associated with low blood glucose levels, and is probably the consequence of a behavioral aberration (i.e., the tendency of premenstrual women to chose high-carbohydrate diets, which potentiate insulin secretion) rather than the cause; the mood and appetitive changes of PMS are poorly correlated with the tissue swelling; and subhuman primates who are presumably exempt from the psychodynamic or social complexities of human life also exhibit characteristic behavioral changes premenstrually.

There have been many treatments suggested for overcoming or reducing the symptoms of PMS. These include carbohydrate-free diets, vitamin supplements, ovarian hormones, detoxifying agents, irradiation of the ovaries and pituitary, and use of diuretics. These approaches have all had limited success, however.

Late Luteal Phase Dysphoric Disorder (LLPDD) is the current term associated with Premenstrual Syndrome (PMS). Many females report a variety of physical and emotional changes associated with specific phases of the menstrual cycle. For most of these females, these changes are not severe, cause little distress, and have no effect on social or occupational functioning. In contrast, the essential feature of LLPDD is a pattern of clinically significant emotional and behavioral symptoms that occur during the last week of the luteal phase and remit within a few days after the onset of the follicular phase. In most females, these symptoms occur in the week before and remit within a few days after the onset of menses.

LLPDD is diagnosed only if the symptoms are sufficiently severe to cause marked impairment in social or occupational functioning and have occurred during a majority of menstrual cycles in the past year.

Among the most commonly experienced symptoms are marked affective lability (e.g., sudden episodes of tearfulness, sadness, or irritabiliy), persistent feelings of irritability, anger, or tension, feelings of depression, and self-deprecating thoughts. Also common are decreased interest in usual activities, fatigue and loss of energy, a subjective sense of difficulty in concentration, changes in appetite, craving for specific foods (especially carbohydrates), and sleep disturbance. Other physical symptoms, such a breast tenderness or swelling, headaches, Joint or muscle pain, a sensation of bloating, and weight gain, also may be present.

Generally, non-steroidal anti-inflammatory drugs are administered to LLPDD patients, but these only are effective for some of the physical symptoms. The physical manifestations of PMS, if severe, may be treated symptomatically. Water retention may be relieved by diet or antidiuretic medication, but severity of water retention does not always correlate with psychological symptoms. Recent studies have suggested that spironolacture (Aldactone, Searle) may also be effective in relieving depression and crying spells.

Other drugs, including progesterone, lithium carbonate, thiazide, diuretics, antidepressants and bromocyptome (Parlodel®, Sandoz), have been tried with uncertain success.

U.S. Pat. No. 5,389,670 describes the use of certain benzothiophenes for treatment of LLPDD/PMS.

In view of the drawbacks and inadequacies with existing methods of treating PMS/LLPDD, new therapies are sought.

The terms peri-menopausal refers to that time in a women's life between pre-menopause (the reproductive years) and post-menopause. This time period is usually between the ages of 40–60, but more often several years on either side of 50 years of age. This period is characterized by a rapid change in the hormonal balance in a woman. Although many different hormones are subject to rapid fluctuation during this time, the most notable are sex related hormones and in particular estrogens and to a lesser extent progestins. The cause of this fluctuation is the natural and time dependent cessation of ovian function. The hallmark of the ending of the peri-menopausal period and the beginning of the post-menopausal period is the cessation of ovian function or its inability to regulate the previously normal ovulation cycle in the woman. This cessation of function is clinically marked by the cessation of menses of a period of one year or more. The time period over which this cessation of ovian function persists, i.e., the peri-menopausal time, is usually not a sudden or rapid event. The peri-menopausal state can last from a few months to more typically a year or more.

As mentioned before the peri-menopause is marked by fluctuations in the woman's hormonal composition, and these fluctuations are marked with many sequelae. Sometimes these sequelae pass without undo problems for the woman; however, they are often a source of moderate to severe discomfort and concern and are occasionally the source of pathological or even life threatening events.

It Is these sequelae in the peri-menopause time which define the syndrome. A list of common, though highly idiosyncratic, sequelae resulting from entering the peri-menopause are: hot flashes and sweats, atrophic vaginitis, headache, dizziness, lack of concentration, irritability, loss of libido, joint pain, sleeplessness, apathy, lassitude, muscular weakness, and palpitations. ("The Menopause", Ed. R. J. Beard, University of Park Press, 1976, Chapter 11). In addition, there has been described a "menopausal or peri-menopausal syndrome" marked with depression. Although there is some controversy as to whether this is a true psychiatric syndrome or not, the peri-menopause is a contributing factor. ("Harrison's principles of Internal Medicine", Ed. N.J. Isselbcher, et al., 9th ed., McGraw-Hill Book Co., 1980 pp. 1782–1783). In extreme cases, some of these sequelae in some woman are pathological (such as fluid retention and imbalance) and even life-threatening, especially in those women predisposed to the effects of depression. However, for most women, a major cause of discomfort and concern lies not so much in the occurrence of one or more of these events, but the length of time which they must bear them and their unpredictable nature.

Since it would be unreasonable to believe that any treatment can turn back the course of aging, the clinical approach to the treatment of peri-menopausal syndrome has been one of amelioration. Specifically, the peri-menopausal woman in need of treatment is given a deescalating protocol of exogenous estrogen. This has the effect of bringing the patient slowly to the state of post-menopause, because although the exogenous estrogen effectively treats the symptoms of peri-menopause, it does not stop the inexorable decline in ovian function. Often, this de-escalation therapy requires a protracted period of time (as much as several years, in extreme cases) in order to a protracted period of time (as much as several years, in extreme cases) in order to allow the ovian function to cease by the time the exogenous estrogen is terminated. Although this therapy is effective and approved, it does carry many side-effects.

The side-effects usually associated with estrogen therapy are due not only to the estrogen, but also with the concomitant progestins. In most cases, women with a uterus must be given estrogen and a progestin either together or more commonly in a cyclic protocol. The reason for this co-administration is to reduce the risk of endometrial cancer which estrogen given alone posses. The effects of the progestin are often poorly tolerated by many women, causing depression or even negating the salutary effects of the estrogen. The estrogen, itself, often causes unpleasant side-effects such as water retention, weight gain, hypertension, etc. The result is often non-compliance of the patient with the therapy and the subsequent suffering of the peri-menopausal symptoms.

Ideally, an improved therapy would be an agent which would ameliorate the symptoms of peri-menopausal syndrome, but would avoid or lessen the side-effects. Additionally, this ideal therapy would also reduce the period of time to bring the woman into a stable, post-menopausal state. U.S. Pat. No. 5,391,557 describes a treatment for peri-menopausal syndrome comprising administration of certain benzothiophene compounds.

The process of blood coagulation, thrombosis, is triggered by a complex proteolytic cascade leading to the formulation of thrombin. Thrombin proteolytically removes activation peptides from the Aα and Bβ-chains of fibrinogen, which is soluble in blood plasma, initiating insoluble fibrin formation.

Anti-coagulation is currently achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because certain coagulation assays are believed to be associated with efficacy and safety, heparin levels are typically monitored with coagulation assays (particularly the activated partial thromboplastin time (APTT) assay). Coumarins impede the generation of thrombin by blocking the post translational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time assay).

To better understand the invention, the following brief description of the coagulation enzyme system is provided. The coagulation system, sometimes referred to as the "cascade", is best looked at as a chain reaction involving the sequential activation of zymogens into active serine proteases which eventually lead to the production of the enzyme, thrombin. Thrombin, through limited proteolysis, converts plasma fibrinogen into the insoluble gel, fibrin. Two key events in the coagulation cascade are the conversion of clotting Factor X to Xa by clotting factor IXa and the conversion of prothrombin into thrombin by clotting factor Xa.

Both of these reactions occur on cell surfaces, most notably the platelet endothelial cell surfaces, and both reactions require cofactors. The major cofactors, factors V and VIII, circulate as relatively inactive precursors, but when the first few molecules of thrombin are formed, thrombin activates, by limited proteolysis, the cofactors. The activated cofactors, Va and VIIIa, accelerate, by about three orders of magnitude, both the conversion of prothrombin into thrombin and the conversion of factor X to factor Xa.

Activated protein C overwhelmingly prefers two plasma protein substrates which it hydrolyzes and irreversibly destroys. These plasma protein substrates are the activated forms of clotting cofactors V and VIII (cofactors Va and VIIIa, respectively). Activated protein C only minimally degrades the inactive precursors, clotting factors V and VIII. In dogs, activated protein C has been shown to sharply increase circulating levels of the major physiological fibrinolytic enzyme, tissue plasminogen activator.

The activation of protein C, however, involves thrombin, the final serine protease in the coagulation cascade, and an endothelial cell membrane-associated glycoprotein, thrombomodulin. Thrombomodulin forms a tight 1:1 stoichiometric complex with thrombin. Thrombomodulin, when complexed with thrombin, modifies substantially the functional properties of thrombin. Thrombin, in the coagulation pathway, normally clots fibrinogen, activates platelets, and converts clotting cofactors V and VIII to their activated forms, Va and VIIIa. Thrombin, alone, acts to activate Protein C, but only very slowly and inefficiently. In contrast, thrombin, when in the a 1:1 complex with thrombomodulin, fails to clot fibrinogen, does not activate platelets, and does not convert clotting factors V and VIII to their activated forms. The thrombin:thrombomodulin complex promotes the activation of protein C with the rate constant of protein C activation being as great as 20,000-fold higher for the thrombin:thrombomodulin complex than the rate constant for thrombin alone.

Activated protein C, therefore, is an antithrombotic agent with a wider therapeutic index than other anticoagulants, such as heparin and the oral hydroxycoumarin-type anticoagulants, such as warfarin. Neither protein C nor activated protein C is effective until thrombin is generated at some local site. Activated protein C is virtually Ineffective without thrombin, because thrombin is needed to convert clotting factors V to Va and VIII to VIIIa. As noted, the activated forms of these two cofactors are the preferred substrate for activated protein C. The protein C zymogen, when infused Into patients, will remain inactive until thrombin is generated. Without the thrombomodulin:thrombin complex, the protein C zymogen is converted into activated Protein C at a very slow rate.

U.S. Pat. No. 5,476,862 describes a method for increasing thrombomodulin expression employing certain benzothiophene compounds.

Uterine fibrosis is an old and ever present clinical problem which goes under a variety of names, including uterine hypertrophy, uterine ileomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formulation of abdominal adhesions and infections. In some patients, initial surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis.

U.S. Pat. No. 5,457,116 describes a method for inhibiting uterine fibrosis by treatment with certain benzothiophene compounds.

Autoimmune diseases involve aberrant regulation of cellular and humoral mediated immunity and are frequently associated with abnormal or enhanced T cell, B cell and macrophage effector functions directed towards self antigens. The activation of these cellular components towards self antigens is believed related to the break in feedback mechanisms associated with self tolerance. Autoimmune diseases encompass a whole spectrum of clinical entities and despite the differences in the target organ have many similarities. These include their preponderance in females of child bearing age with a female to male ratio varying from 50:1 In Hashimoto's thyroiditis to 10:1 in Systemic lupus erythematosus (SLE) to 2:1 in Myasthenia gravis (Ahmed et al., Am J. Path., 121:531 (1985)). In addition, these diseases are all characterized by the chronicity, the tendency of clinical remission and "flare ups" for poorly understood reasons, and the involvement of other organs. While the presence of autoantibodies, inappropriate expression of class II antigens, macrophage activation and T cell infiltration to the target organ have been described in essentially all of the autoimmune diseases, neither the triggering mechanisms which result in disease activation not disease progression are well understood. Accordingly, therapy for these diseases is largely unsatisfactory and involves the use of gold salts, methotrexate, antimalarials, glucocorticoids (methylprednisolone), and other immunosuppressives as well as plasmaphoresis and attempts at inducing tolerance. Treatment of autoimmune diseases has not Improved significantly over the past decade and primarily is associated with the use of nonsteroidal and steroidal anti-inflammatory agents to treat the symptoms of the disease. Clearly while suppression of the specific immune response directed against the host is necessary, generalized immunosuppression as with glucocorticoids has major liabilities in terms of side effect profile and the propensity of the immunosuppressed patient to be at greater risk for other infectious and non-infectious diseases.

Polymorphonuclear leukocytes (PMNL) play a regulatory role in inflammatory diseases. These cells, when activated, synthesize and release oxygen-centered molecules, chemoattractants, and hydrolytic enzymes. There is evidence that the oxygen-centered molecules play a detrimental role in a number of diseases such as chronic inflammatory diseases, rheumatoid arthritis, SLE, and others. In the case of an autoimmune disease, SLE, for example, the initiation of an inflammatory response are self antigen stimulating one's host neutrophils or PMNLs to secrete strong oxidants which damage surrounding cells and tissue.

Estrogen appears to be involved with autoimmune diseases although its role in disease progression or regression is complex and dependent on the nature of the autoimmune disease. Estrogen for example appears to have ameliorating effect on rheumatoid arthritis while having an exacerbating effect on systemic lupus (Chander & Spector; Ann. Rheum. Dis. 50:139). As reported by Jansson (*Free Rad Res Comms,* 14(3), 195–208, (1991), incorporated herein by reference), estrogen increased the activity of an enzyme generated by PMNLS, myeloperoxidase, which regulates the production of oxidants from hydrogen peroxide. This enzyme converts hydrogen peroxide to hypochlorous acid, a strong oxidant. By increasing the enzyme's activity, and thus the presence of hypochlorous acid, the likelihood of increased oxidative stress on tissues, cells and various macromolecules in chronic inflammatory/autoimmune diseases is enhanced.

EP 664 125 A1 reports that inhibition of myeloperoxidase may be accomplished by treatment with certain 3-aroyl benzothiophines. Excess myeloperoxidase is associated with conditions which include systemic lupus erythematosis, Hashimoto's thyroiditis, myasthenia gravis, rheumatoid arthritis and multiple sclerosis.

2-Phenyl-3-aroylbenzothiophene derivatives are reported to inhibit thrombin; see EP 0664126 A1.

Estrogen has been demonstrated to have a suppressive role on T cell function and yet an immunostimulatory effect on B cells. Therefore, estrogen-like compounds should prove beneficial in diseases associated with activated T cells including rheumatoid arthritis, multiple sclerosis, Guillan Barre syndrome and Hashimoto's thyroiditis through inhibition of T cell function (Holmadahl, J. Autoimmun. 2:651 (1989).

In addition to the suppressive effects of estrogen on T cells, estrogen may have additional protective roles. Marui et al., (J. Clin. Invest. 92:1866 (1993)) have recently reported that antioxidants suppress endothelial expression of VCAM-1. VCAM-1 is the ligand for VLA4, the T cell and macrophage integrin associated with trafficking of these cells out of the vasculature and into the perivascular space and target organs. As estrogen is an antioxidant, it would be anticipated that estrogen and related analogs will inhibit VLA-4 dependent trafficking of cells and thus hinder the immune cascade associated with autoimmune mediated disease.

Estrogen plays a detrimental role in other autoimmune diseases including systemic lupus and glomerulonephritis, diseases associated with immune complexes. While the mechanism(s) responsible for estrogen mediated disease progression are not known, the ability of estrogen to increase Fc mediated phagocytosis (Friedman et al., J. Clin. Invest. 76:162 (1985), and class II antigen expression and IL-1 production by macrophages from estrogen treated rodents (Flynn, Life Sci., 38:2455 (1986) has been reported. Enhancement of these macrophage mediated effector functions would be expected to contribute towards the immune cascade associated with self destruction.

It is reported in EP 664123 A1 that certain 2-phenyl-3-aroylbenzothiophenes are effective inhibitors of autoimmune diseases.

Premenopausal women are at lower risk of coronary heart disease than their male counterparts, and it has been shown that estrogen treatment protects against cardiovascular disease in postmenopausal women. Hale and Kloner have shown that acute pretreatment with estradiol reduced myocardial infarct size caused by occlusion of the coronary artery in both male and female rabbits. J. Am. Coll. Cardiol. 25, 189A (199).

In males, small amounts of estrogen are produced by aromatization of testosterone both in the testes and peripheral tissues. Although present in only small amounts, generally less than one-fourth to one-tenth that in premenopausal women, estrogen may play a role in the regulation of the male hypothalamic pituitary gonadaxis, bone development, development of the prostate and metabolic function. In the hypothalamus, conversion of testosterone to estrogen results in negative feedback on gonadotropin releasing hormone and subsequent gonadotropin release. Estrogens thus normally reduce circulating testosterone and anti-estrogens result in corresponding increases. As men age, the proportion of fat to lean tissue gradually increases. Aromatization of testosterone in fat may lead to gradually increased estrogen to testosterone ratios and negative feedback that reduces total testosterone levels.

Hypogonadism is recognized as a common occurrence in older males. A number of studies have suggested that hypogonadism may result in some of the observed decrements in muscle and skeletal mass associated with advancing age. Recent studies have suggested that androgen therapy produces a small but significant improvement in muscle strength in eugonadal males. Testosterone deficiency has been associated with hip fracture, and bone mass has been correlated with testosterone levels in older persons.

Males who received testosterone had a significant increase in bioavailable testosterone concentration, hematocrit, right hand muscle strength and osteocalcin concentration. They had a decrease in cholesterol (without a change in HDL-cholesterol) levels and decreased BUN/Creatinine ratios. Morley, et al. JAGS 41:149–150 (1993).

The term "inhibit" is defined to include its generally accepted meaning which includes prophylactically treating a subject to prevent the occurrence of one or more of these disease states, holding in check the symptoms of such a disease state, and/or treating such symptoms. Thus, the present methods include both medical therapeutic and/or prophylactic treatment, as appropriate.

The methods of this invention are practiced by administering to an individual in need of treatment an effective amount of a compound formula I.

Compounds of formula I are described as being effective in treatment of prostate disease, breast cancer, osteoporosis, endometriosis, cardiovascular disease and hypercholesterolemia in commonly owned U.S. patent application Ser. No. 08/369,954 which is hereby incorporated by reference.

The terms $C_1$–$C_3$ chloroalkyl and $C_1$–$C_3$ fluoroalkyl include methyl, ethyl, propyl and isopropyl substituted to any desired degree with chlorine or fluorine atoms, from one atom to full substitution. The term $C_5$–$C_7$ cycloalkyl includes cyclopentyl, cyclohexyl and cycloheptyl.

Halo means chloro, bromo, iodo and fluoro. Aryl (Ar) includes phenyl and naphthyl optionally substituted with one to three substituents independently selected from $R^4$ as defined above. DTT means dithiothreitol. DMSO means dimethyl sulfoxide. EDTA means ethylene diamine tetra acetic acid.

Estrogen agonists are herein defined as chemical compounds capable of binding to the estrogen receptor sites in mammalian tissue, and mimicking the actions of estrogen in one or more tissues.

Estrogen antagonists are herein defined as chemical compounds capable of binding to the estrogen receptor sites in mammalian tissue, and blocking the actions of estrogen in one or more tissues.

One of ordinary skill will recognize that certain substituents listed in this invention will be chemically incompatible with one another or with the heteroatoms in the compounds, and will avoid these incompatibilities in selecting compounds of this invention. Ukewise certain functional groups may require protecting groups during synthetic procedures which the chemist of ordinary skill will recognize.

The chemist of ordinary skill will recognize that certain compounds of this invention will contain atoms which may be in a particular optical or geometric configuration. All such isomers are included in this invention; exemplary levorotatory isomers in the cis configuration are preferred. Likewise, the chemist will recognize that various pharmaceutically acceptable esters and salts may be prepared from certain compounds of this invention. All of such esters and salts are included in this invention.

The remedies for the conditions and diseases for use in the methods of this invention can be prepared by the methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutical effect; for example, about 0.1 mg to 50 mg in unit dosage for both oral and parenteral administration.

The active ingredient may be usually administered once to four times a day with a unit dosage of 0.1 mg to 50 mg in human patients, but the above dosage may be properly varied depending on the age, body weight and medical condition of the patient and the type of administration. A preferred dose is 0.25 mg to 25 mg in human patients. One dose per day is preferred.

Compounds used in the methods invention are readily prepared by the reactions illustrated in the schemes below.

Certain compounds of formula I are conveniently prepared from an unsaturated intermediate

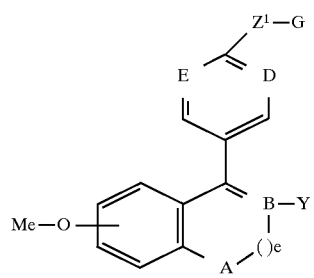

by hydrogenation with a noble metal catalyst in a reaction inert solvent. Pressure and temperatures are not critical and hydrogenation is normally accomplished in a few hours at room temperatures at 20–80 psi hydrogen pressure.

The hydrogenated product is isolated, purified if desired, and the ether group is cleaved with an acidic catalyst in a reaction inert solvent at a temperature between 0° C. to 100° C. depending on the acidic catalyst used. Hydrogen bromide at elevated temperatures, boron tribromide and aluminum chloride at 0° C. to ambient temperature have been found to be effective for this reaction.

The product, Formula I is isolated and purified by standard procedures.

Intermediates of Formula II where A is $CH_2$, and B, D and E are CH are described in U.S. Pat. No. 3,274,213; J. Med. Chem 10, 78 (1967); J. Med. Chem 10, 138 (1967); and J. Med. Chem. 12, 881 (1969), the disclosures of which are herein incorporated by reference. They can also be prepared by procedures described below.

The preparation of the compounds of Formula I where e=1, A=$CH_2$, $Z^1$=$OCH_2CH_2$, G=cycloalkylamine, B=CH is shown in Scheme 1. Compounds 1-2, where D and E are CH are made by alkylation of 4-bromophenol with the corresponding N-chloroethylamine using potassium carbonate as base in a polar aprotic solvent like dimethylformamide at elevated temperatures. A preferred temperature is 100° C. Compounds 1-2 where D or E or both are N are synthesized using a nucleophilic displacement reaction performed on dibromides (1-1) using hydroxy ethyl cycloalkylamines under phase transfer conditions to afford bromo amines (1-2). Synthesis, 77, 573 (1980). Following halogen metal exchange using n-butyllithium or magnesium metal, bromo amines (1-2) yield the corresponding lithium or magnesium reagents which are allowed to react at low temperature in the presence of cesium chloride preferably (without cesium chloride the reaction also proceeds) with 6-methoxy-1-tetralone to afford either carbinols (1-3) or styrenes (1-4) after acidic workup. Treatment of either carbinols (1-3) or styrenes (1-4) with a brominating agent such as pyridinium bromide perbromide affords bromo styrenes (1-5). Aryl or heteroaryl zinc chlorides or aryl or heteroaryl boronic acids react with bromides (1-5) in the presence of a palladium metal catalyst like tetrakis triphenyl phosphine palladium (0) to yield diaryl styrenes (1-6). [Pure & Applied Chem. 63, 419,(1991) and Bull. Chem. Soc. Jpn. 61, 3008–3010, (1988)] To prepare the preferred compounds the substituted phenyl zinc chlorides or substituted phenylboronic acids are used in this reaction. The aryl zinc chlorides are prepared by quench of the corresponding lithium reagent with anhydrous zinc chloride. The aryl boronic acids, that are not commercially available, are prepared by quenching the corresponding aryl lithium reagent with trialkyl borate, preferably the trimethyl or triisopropyl borate, followed by aqueous acid workup. Acta Chemica Scan. 47, 221–230 (1993). The lithium reagents that are not commercially available are prepared by halogen metal exchange of the corresponding bromide or halide with n-butyl or t-butyllithium. Alternately, the lithium reagent is prepared by heteroatom facilitated lithiations as described in Organic Reactions, Volume 27, Chapter 1. Catalytic hydrogenation of 1-6 in the presence of palladium hydroxide on charcoal, for example, affords the corresponding dihydro methoxy intermediates which were subsequently demethylated using boron tribromide at 0° C. in methylene chloride or 48% hydrogen bromide in acetic acid at 80°–100° C. to afford target structures (1-7). These compounds are racemic and can be resolved into the enantiomers via high pressure liquid chromatography using a column with a chiral stationary phase like the Chiralcel OD columns. Alternately optical resolution can be carried out by recrystallzation of the diastereomeric salts formed with optically pure adds like 1,1'-binapthyl-2,2'-diyl hydrogen phosphate (see Example 8).

The cis compounds (1-7) can be isomerized to the trans compounds on treatment with base (see Example 2).

When D and/or E is nitrogen the intermediates (Formula II) and compounds of Formula I may be prepared from the corresponding dihalopyridines or pyrmidines as illustrated in Scheme 1 and as fully described for 6-phenyl-5-[6-(2-pyrrolidin-1-yl-ethoxy) pyridin-3-yl]-5,6,7,8tetrahydronaphthalen-2-ol in Example 6.

The methyl ether of the compound of Formula I where e=1, A=$CH_2$, $Z^1$=$OCH_2CH_2$, G=pyrrolidine, D,E, B=CH, Y=Ph can also be conveniently prepared by a first step of hydrogenation of nafoxidine (Upjohn & Co., 700 Portage Road, Kalamazoo, Mich. 49001) in a reaction inert solvent in the presence of a nobel metal catalyst. Pressure and temperature are not critical; the reaction is conveniently run in ethanol at room temperature for approximately 20 hours at 50 psi.

The second step is cleavage of the methoxy group which is accomplished conveniently at room temperature with an acidic catalyst such as boron tribromide in a reaction inert solvent or at 80°–100° C. with hydrogen bromide in acetic acid. The product is then Isolated by conventional methods and converted to an acid salt if desired.

SCHEME 1

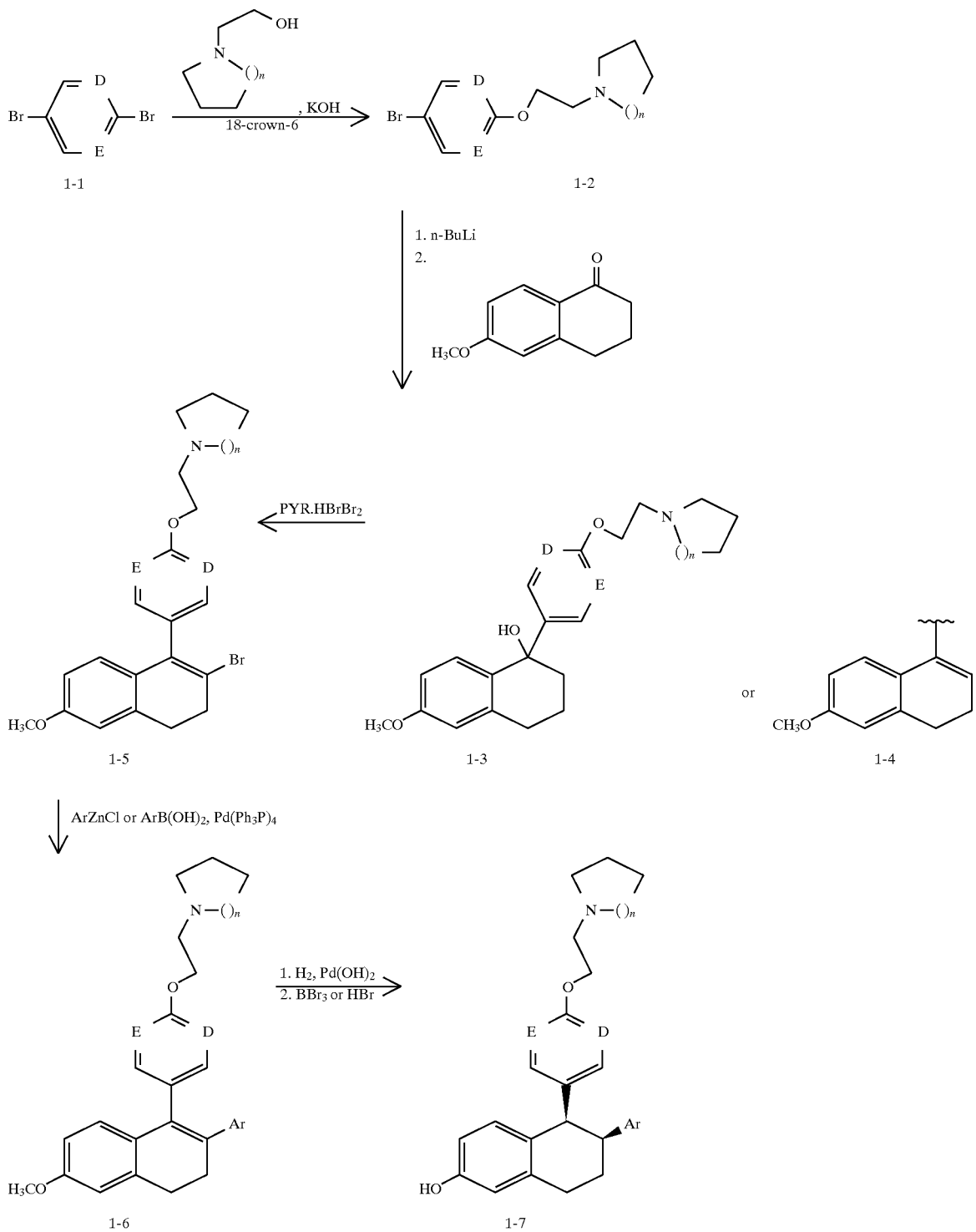

Compounds of formula I wherein B is nitrogen are prepared by the procedures illustrated in Scheme 2 and 3 and Examples 3–5 and 10–12.

The synthesis of compounds of Formula I where B=N is shown in Scheme 2. Aryl acid chlorides (2-1) on treatment with primary amines afford aryl secondary amides (2-2), which are reduced with lithium aluminum hydride in ethereal solvents to yield secondary amines (2-3). Subsequent acylation of (2-3) with aroyl acid chlorides leads to tertiary amides (2-4), which are cyclized in hot phosphorus oxychloride to yield dihydro isoquinolinium salts (2-5). Reduction with sodium borohydride to alkoxytetrahydro isoquinolines; followed by boron tribromide demethylation in methylene chloride affords the target structures.

SCHEME 2

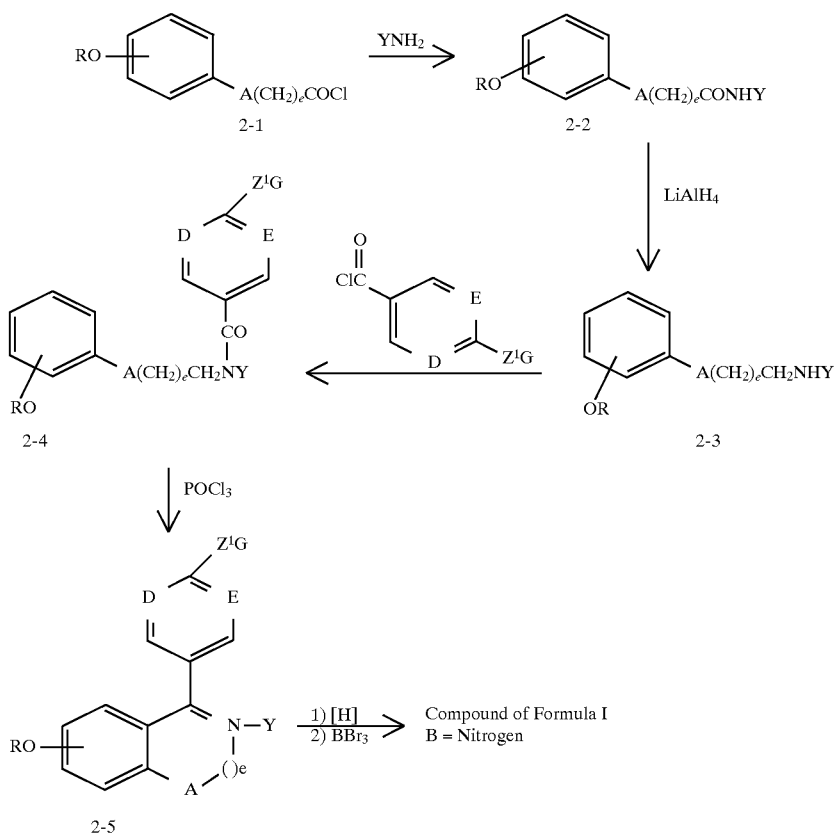

The synthesis of the compounds of Formula I where B=N is also described below in Scheme 3. Secondary amines (3-1) on acylation with benzyloxyaroyl chlorides (3-2) afford tertiary amides (3-3) which on cyclization with hot phosphorous oxychloride yield dihydro isoquinoline salts (3-4). Sodium borohydride reduction of (3-4) followed by debenzylation with aqueous hydrochloric acid affords isoquinolines (3-5), which are alkylated with the appropriately functionalized chlorides and demethylated with boron tribromide to yield the desired target structures.

SCHEME 3

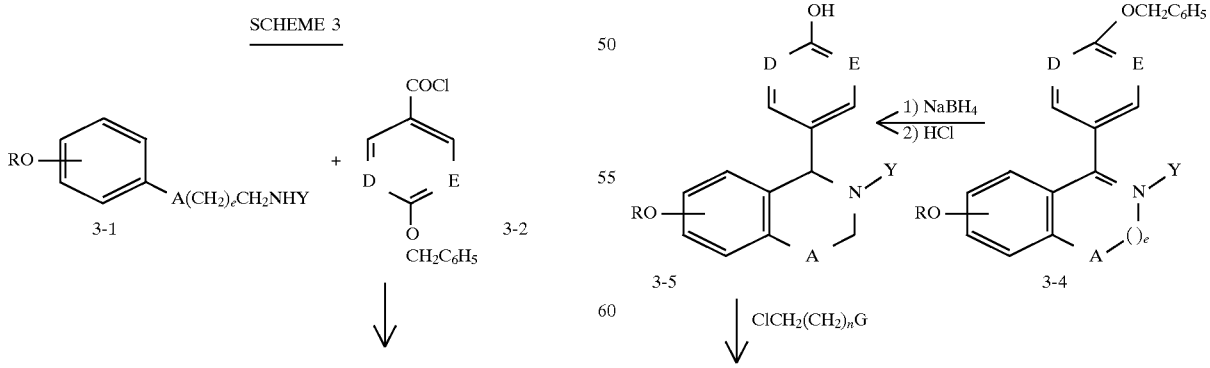

-continued
SCHEME 3

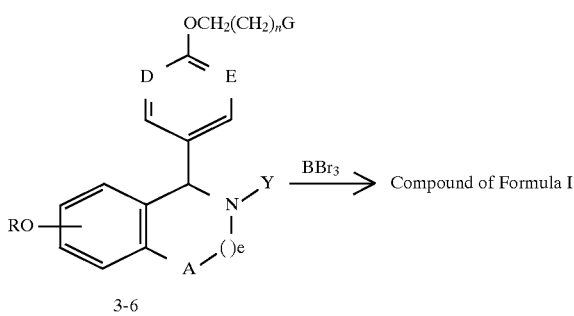

3-6

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate,β-hydroxybutyrate, butyne-1,4dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the methods herein described. The following nonlimiting test examples illustrate the methods of the present invention.

For the methods of the present invention, compounds of Formula I are administered continuously, or from 1 to 4 times daily.

As used herein, the term "effective amount" means an amount of compound of the methods of the present invention which is capable of inhibiting the symptoms of the pathological conditions herein described. The specific dose of a compound administered according to this invention will, of course, be determined by the particular circumstances surrounding the case including, for example, the compound administered, the route of administration, the state of being of the patient, and the severity of the pathological condition being treated. A typical daily dose will contain a nontoxic dosage level of from about 0.25 mg to about 100 mg/day of a compound of the present invention. Preferred daily doses generally will be from about 10 mg to about 40 mg/day.

The compounds of this invention can be administered by a variety of routes including oral, rectal, transdermal, subucutaneous, intravenous, intramuscular, and intranasal. These compounds preferably are formulated prior to administration, the selection of which will be decided by the attending physician. Typically, a formula I compound, or a pharmaceutically acceptable salt thereof, is combined with a pharmaceutically acceptable carrier, diluent or excipient to form a pharmaceutical formulation.

The total active ingredients in such formulations comprises from 0.1% to 99.9% by weight of the formulation. By "pharmaceutically acceptable" it is meant the carrier, diluent, excipients, and/or salt must be compatible with the other ingredients of the formulation, and not deleterious to the recipient thereof.

Pharmaceutical formulations containing a compound of formula I can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate agents for retarding dissolution such as paraffin resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by Intramuscular, subcutaneous or intravenous routes.

Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I generally will be administered in a convenient formulation. The following formulation examples only are illustrative and are not intended to limit the scope of the present invention.

In the formulations which follow, "active ingredient" means a compound of formula I, or a salt thereof.

Formulation 1: Gelatin Capsules

Hard gelatin capsules are prepared using the following:

| Ingredient | Quantity (mg/capsule) |
|---|---|
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
|---|---|
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–400 mg of active ingredient are made up as follows:

Formulation 3: Tablets

| Ingredient | Quantity (mg/tablet) |
|---|---|
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of medicament per 5 ml dose are made as follows:

Formulation 4: Suspensions

| Ingredient | Quantity (mg/5 ml) |
|---|---|
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The medicament is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
|---|---|
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
|---|---|
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
|---|---|
| Active ingredient | 20 mg |
| Isotonic saline | 1,000 mL |

The solution of the above ingredients is intravenously administered to a patient at the rate of about 1 mL per minute.

Assays For Inhibition of Alzheimer's Disease

Assays for compounds effective in treatment of AD are described in EP 0659418 A1.

Amylins may be purchased from Bachem, Inc. (Torrance, Calif.), Peninsula Laboratories, Inc. (Belmont, Calif.), Sigma Chemicals (St. Louis, Mo.). Amyloid-$\beta$(1-40) and reverse $\beta$-amyloid peptide (40-1) may be purchased from Bachem, Inc. $\beta_2$-microglobulin may be purchased from Sigma Chemicals (St. Louis, Mo.).

Stock solutions of peptides (1 mM) are freshly prepared in pyrogen-free sterile water and diluted to the indicated concentrations in defined culture media. Rat hippocampal cultures (10–14 days in vitro) are treated with peptides or vehicle for four days. The viability of the rat cortical cultures is visually assessed by phase contrast microscopy and quantified by measuring lactate dehydrogenase (LDH) released into the culture media.

Assay 1

Primary rat hippocampal neurons are cultured in vitro with standard cell culture techniques. Amyloid-beta (A$\beta$) peptide is added to cultured cells at a normally toxic concentration of 25–50 $\mu$M. After 4 days of treatment, viability is assessed by measurement of lactate dehydrogenase (LDH) released into culture medium. Lactate dehydrogenase (LDH) is measured in 20 $\mu$l aliquots of conditioned defined-DMEM using a standard 340 nm kinetic LDH assay (Sigma Catalog Number #228-20) in a 96 well format. Assays are performed at 37° C. in a PC-driven EL340 Microplate Biokinetics plate reader (Bio-Tek Instruments) using Delta Soft II software (v. 3.30B, BioMetallics, Inc.) for data analysis. Quality control standards containing normal and elevated levels of serum LDH (for example, Sigma Enzyme Controls 2N and 2E) are run with every assay. Results are expressed as units of LDH/L where 1 unit is defined as the amount of enzyme that will catalyze the formation of 1 micromole of nicotinamide adenine dinucleotide per minute under conditions of the assay. For protection studies, a compound of formula 1 is added to cultures prior to and/or concurrently with the amyloid-β treatment.

Activity of the compounds of formula 1 is illustrated by a decrease in LDH released into the media (a neurotoxic indicator), as compared to control.

Assay 2

Between five and fifty rats are subjected to 15 minutes of four vessel occlusion to induce global ischemia. A compound of the invention is administered to experimental and control animals prior to, concurrent with and/or up to several hours after 15 minutes of occlusion. Animals are sacrificed 3 days after the ischemic insult and neuronal damage in the hippocampus and striatum is then visually assessed by standard histologic techniques.

Activity of the compounds of formula 1 is illustrated by a decrease in neuronal damage.

Assay 3

Five to fifty women are selected for the clinical study. The women are post-menopausal, i.e., have ceased menstruating for between 6 and 12 months prior to the study's initiation, have been diagnosed with early stage Alzheimer's Disease (AD), are expected to have worsening symptoms of AD within the study period, but are in good general health otherwise. The study has a placebo control group, i.e., the women are divided into two groups, one of which receives the active agent of this invention and the other receives a placebo. The patients are benchmarked as to memory, cognition, reasoning, and other symptoms associated with AD. Women in the test group receive between 10–100 mg of the active agent per day by the oral route. They continue this therapy for 6–36 months. Accurate records are kept as to the benchmarked symptoms in both groups and at the end of the study these results are compared. The results are compared both between members of each group and also the results for each patient are compared to the symptoms reported by each patient before the study began. Activity of the test drug is illustrated by an attenuation of the typical cognitive decline and/or behavioral disruptions associated with AD.

Utility of the compounds of formula I is evidenced by activity in at least one of the above assays.

TEST PROCEDURE FOR PMS/LLPDD

Three to fifty women are selected for the clinical study. The women have regular menses, are in good general health, and suffer from one or more of the above mentioned PMS/LLPDD symptoms. Because of the somewhat idiosyncratic and subjective nature of these symptoms, the study has a placebo control group, i.e., the woman are divided into two groups, one of which receives the active agent of this invention and the other receives a placebo. Women in the test group receive between 10–100 mg of the drug per day by the oral route. They continue this therapy for 1–3 months. Accurate records are kept as to the number and severity of the symptoms in both groups and at the end of the study these results are compared. The results are compared both between members of each group and also the results for each patient are compared to the symptoms reported by each patient before the study began. See U.S. Pat. No. 5,389,670.

Utility of the compounds of the invention for inhibiting the symptoms of PMS/LLPDD is illustrated by the positive impact they have on one or more of the symptoms when used in a study as above.

TEST PROCEDURE FOR INHIBITION OF PERI-MENOPAUSAL SYNDROME

Test 1

A group of 3–20 women between the age of 45–50 years of age are selected as a test group. The women exhibit at least one of the sequelas of impending menopause. A compound of the invention is given in the amount of 10–100 mg/day and the sequelae are closely monitored. The dosing of the compound of the invention continues for a period of three (3) weeks.

Test 2

The same test as in Test 1 is carried out, however, the administration period is for a time of three (3) months.

Test 3

This test is ran as Test 1, except the dosing period is for a period of six (6) months.

Activity, defined as either total cessation of one or more sequelae of the patient, or reduced severity or occurrence thereof, or a more rapid advancement to menopausal state, in any of the above assays indicates that the compounds of the invention are useful in the treatment of peri-menopausal syndrome.

ASSAYS FOR INCREASED THROMBOMODULIN EXPRESSION

The assays below are described in EP 0659427 and U.S. Pat. No. 5,476,862 which is incorporated herein by reference.

Assay 1

To further understand the action(s) of the compounds of formula 1, intimal smooth muscle cells and its role in enhancing anticoagulation of blood, it is necessary to investigate changes in thrombomodulin (TM) activity on the surface of these cell types. The compounds of formula 1 may also be used to reverse/correct any effects of mediators that tend to down regulate TM activity on the surface of these cells.

Approximately 40,000–80,000 early passaged endothelial (arterial, venous, or microvascular), or intimal smooth muscle cells are seeded and grown to confluency in 24-well cell culture plates. The cell monolayer is subsequently washed 2–3 times with either Hank's buffered saline solution (HBSS), or serum-free medium (SFM). For a period of 24 hours, varying concentrations of a compound of formula 1 (ranging from micromolar to subpicomolar) are added to the cells in triplicate. The cells residing in negative control wells are maintained on serum-free medium with an amount of vehicle equivalent among all wells.

The existing method to measure cell surface TM activity is performed by using a two-phase amidolytic assay. During the first phase of the assay, following rinsing of the cells with HBSS or SFM, 0.4 ml SFM containing human protein C (final concentration 11.2 ug/ml) and human aipha-thrombin (final concentration 0.1 NIHU/ml) are added to the monolayer and incubated at 37° C. and 5% $CO_2$. At 15, 30 and 45 minute time points, 100 ul of medium is removed from each well and added to 50 ul of excess hirudin (20 anti-thrombin U/ml) in microtiter wells for 5 minutes at 37° C. in order to arrest further thrombin activity. In the absence of cells, SFM plus protein C and alpha-thrombin, as described above, is used as a negative control and treated similarly.

In the second phase of the assay, 50 ul of 3 mM 2366, a chromogenic substrate of protein C, is added to the conditioned media/hirudin mixture and the $OD_{405}$ is measured by an automatic plate reader to monitor the kinetics of TM activity over a 4 minute period. Upon completion of this kinetic assay, measurement of total protein is performed using the BCA method. The final TM activity is expressed as % increase.

Assay 2

The baboon model of *E. Coli*-induced sepsis as described in U.S. Pat. No. 5,009,889 (incorporated herein by reference) is used to illustrate the compounds of formula 1 effects as antithrombotics and their ability to correct inflammation-induced endothelial dysfunction.

Utility of the compounds of the invention is illustrated by the positive impact on thrombomodulin expression, thrombotic disorder, or Protein C activation rate characteristics displayed by any of the above assays.

TEST FOR INHIBITION OF UTERINE FIBROSIS

Test 1

Between 3 and 20 women having uterine fibrosis are administered a compound of the invention. The amount of compound administered is 0.1 to 100 mg/day, and the period of administration is 3 months.

The women are observed during the period of administration and up to 3 months after discontinuance of the compound for effects on uterine fibrosis.

Test 2

The same procedure is used as in Test 1, except the period of administration is 6 months.

Test 3

The same procedure is used as in Test 1, except the period of administration is 1 year.

Test 4

A. Induction of fibroid tumors in guinea pig.

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice.

Tissue from human leiomyomas are implanted into the peritoneal cavity and or uterine myometrium of sexually mature, castrated female nude mice. Exogenous estrogen are supplied to induce growth of the explanted tissue. In some cases the harvested tumor cells are cultured in vitro prior to implantation. Treatment consisting of a compound of the invention or vehicle is supplied by gastric lavage on a daily basis for 3–16 weeks and Implants are removed and measured for growth or regression. At the time of sacrifice, the uteri is harvested to assess the status of the organ.

Test 5

A. Tissue from human uterine fibroid tumors is harvested, and maintained in vitro as primary nontransformed cultures. Surgical specimens are pushed through a sterile mesh or sieve or alternately teased apart from surrounding tissue to produce a single cell suspension. Cells are maintained in media containing 10% serum and antibiotics. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention and vehicle. Levels of steroid hormone receptors are assessed weekly to determine whether important cell characteristics are maintained in vitro. Tissue from 5–25 patients is utilized.

Activity in at least one of the above tests indicates the compounds of the invention are of potential in the treatment of uterine fibrosis.

ASSAYS TO SHOW INHIBITION OF MYELOPEROXIDASE

Assay 1

In order to investigate the myeloperoxidase activity inhibiting properties of compounds of formula 1, Assays 1 and 2, as set out in Jansson (supra.), are employed.

In this assay, human PMN leukocytes are stimulated with estriol to increase myeloperoxidase activity in the presence of added hydrogen peroxide. The conversion of luminol by hypochlorous acid is measured by chemiluminescence. The reaction mix consists of cells ($10^6$), agent or compound of formula 1 (1 $\mu$M), hydrogen peroxide (0.1 mM), and luminol (0.2 mM) incubated at 37° C.

Estrogen and its analogs stimulate myeloperoxidase activity. Compounds of formula 1 antagonize the estriol stimulated chemiluminescence.

Assay 2

Purified human myeloperoxidase is incubated with agent (estrogen or a compound of formula 1), in the presence of luminol at 37° C. The substrate, hydrogen peroxide, is added and the chemiluminescence measured. The reaction mix is human MPE (250 ng), agent or a compound of formula 1 (10 $\mu$M, titrated), hydrogen peroxide (1 mm), and luminol (0.2 mm).

Estrogen and its analogs have little or no effect on MPE activity, however, compounds of formula 1 reduce the activity of purified MPE.

Assay 3

Five to fifty women are selected for the clinical study. The women suffer from SLE or rheumatoid arthritis. Because of the idiosyncratic and subjective nature of these disorders, the study has a placebo control group, i.e., the women are divided into two groups, one of which receives a compound of formula 1 as the active agent and the other receives a placebo. Women in the test group receive between 50–100 mg, of the drug per day by the oral route. They continue this therapy for 3–12 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula 1 is illustrated by the positive impact they have in at least one of the assays described above.

ASSAYS TO SHOW INHIBITION OF THROMBIN

Methods—Effects on Lysis of Human Plasma Clots by t-PA

Human plasma clots are formed in micro test tubes by adding 50 ul thrombin (73 NIH unit/ml) to 100 ul human plasma which contains 0.0229 uCi 125-iodine labeled fibrinogen. Clot lysis is studied by overlaying the clots with 50 ul of urokinase or streptokinase (50, 100, or 1000 unit/ml) and incubating for 20 hours at room temperature. After incubation the tubes are centrifuged in a Beckman Microfuge. 25 ul of supernate is added into 1.0 ml volume of 0.03M tris/0.15M NACl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/ml concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction 1–2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/ plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Ann Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) Is used for all coagulation assay measurements. The prothrombin time (PT) Is measured by adding 0.05 ml saline and 0.05 ml Thromboplastin-C reagent to 0.05 ml test plasma. The activated partial thromboplastin time (APTT) is measured by incubation of 0.05 ml test plasma with 0.05 ml Actin reagent for 120 seconds followed by 0.05 ml $CaCl_2$ (0.02M). The thrombin time (TT) is measured by adding 0.05 ml saline and 0.05 ml thrombin (10 NIH units/ml) to 0.05 ml test plasma. The compounds of formula I we added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley, Inc., Indianapolis, Ind.) are anesthetized with xylazine (20 mg/kg, s.c.) and ketamine (120 mg/kg, s.c.) and maintained on a heated water blanket (37° C). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 ul is pipetted into the cuff to bathe the artery above the thermocouple probe. Arterial occlusion is indicated by a rapid drop in temperature. The time to occlusion is reported in minutes and represented the elapsed time between application of $FeCl_3$ and the rapid drop in vessel temperature (see K. D. Kurz, *Thromb. Res.*, 60:269, 1990).

Spontaneous thrombolysis model

In vitro data suggest that the peptide thrombin inhibitors inhibit thrombin and other serine proteases, such as plasmin and issue plasminogen activator. To assess if the compounds inhibit fibrinolysis in vivo, the rate of spontaneous thrombolysis is determined by implanting a labeled whole blood clot into the pulmonary circulation. Rat blood (1 ml) is mixed rapidly with bovine thrombin (4 IU, Parke Davis) and $^{1.25}$I human fibrinogen (5 $\mu$Ci,ICN), immediately drawn into elastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected cpm} - \text{lung cpm})}{\text{injected cpm}} \times 100$$

The fibrinolytic dissolution of the implanted clot occurs time-dependently (see J. P. Clozel, *Cardiovas. Pharmacol.*, 12:520, 1988).

Coagulation parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 ml) is mixed with saline (0.1 ml) and bovine thrombin (0.1 ml, 30 U/ml in TRIS buffer; Parke Davis) at 37° C. For APTT, plasma (0.1 ml) and APTT solution (0.2 ml, Organon Teknika) are incubated for 5 minutes (37° C.) and $CaCl_2$ (0.025M) is added to start coagulation. Assays are done in duplicate and averaged.

Index of Bioavailability

A measure of bioactivity, plasma thrombin time (TT), serve as a substitute for the assay of parent compound on the assumption that increments in TT resulted from thrombin inhibition by parent only. The time course of the effect of the thrombin inhibitor upon TT Is determined after i.v bolus administration to anesthetized rats and after oral treatment of fasted conscious rats. Due to limitations of blood volume and the number of points required to determine the time course from time of treatment to the time when the response returned to pretreatment values, two populations of rats are used. Each sample population represented alternating sequential time points. The average TT over the time course is used to calculate area under the curve (AUC). The index of bioactivity is calculated by the formula shown below and is expressed as percent relative activity. The area under the curve (AUC) of the plasma TT time course is determined and adjusted for the dose. This index of bioavailability is termed "% Relative Activity" and is calculated as $$\% \text{ Relative Activity} = \frac{AUC \text{ po}}{AUC \text{ iv}} \times \frac{\text{Dose iv}}{\text{Dose po}} \times 100$$

Compounds

Compound solutions are prepared fresh daily in normal saline and are injected as a bolus or are infused starting 15 minutes before and continuing throughout the experimental perturbation. Bolus injection volume is 1 ml/kg for i.v., and 5 ml/kg for p.o. and infusion volume is 3 ml/hr.

Statistics

Results are expressed as means ±SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66°–74° F.; 45–50 percent relative humidity; and lighted from 0600–1800 hours.

Pharmacokinetic model

Test compound is formulated immediately prior to dosing by dissolving in sterile 0.9 percent saline to a 5 mg/ml preparation. Dogs are given a single 2 mg/kg dose of test compound by oral gavage. Blood samples (4.5 ml) are taken from the cephalic vein at 0.25, 0.5, 0.75, 1,2,3,4 and 6 hours after dosing. Samples are collected in citrated Vacutainer tubes and kept on ice prior to reduction to plasma by centrifugation. Plasma samples are derivatized with dinitrophenylhydrazine and analyzed by HPLC (Zorbax SB-C8 column) eluting with methanol/500 mM sodium acetate adjusted to pH 7 with phosphoric acid (60:40, v/v). Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration or test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs is as described in Jackson, et al., Circulation, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$ and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silver-plated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvem, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX if totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombotic agent (e.g. tissue plasminogen activator, streptokinase, APSAC). Reperfusion is followed for 3 hours after administration of test compound. Reocclusion of coronary arteries after successful thrombolysis is defined as zero CBF which persisted for $\geq 30$ minutes.

Hematology and template bleeding time determinations

Whole blood cell counts, hemoglobin, and hematocrit values are determined on a 40-$\mu$A sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described In Jackson, et al., *J. Cardiovasc. Pharmacol.*, 21, 587–599 (1993).

The compounds of the invention 1 are also evaluated in the Template Bleeding Time assay at 0.25, 0.50 and 1.0 mg/kg. hr.

Utility of the compounds of the invention is illustrated of a positive result in any of the above assays.

ASSAYS TO SHOW INHIBITION OF AUTOIMMUNE DISEASE

Assay 1

The procedure as set out in Holmdahl et al., Clin. Exp. Immunol.; 70, 373–378 (1987) (herein incorporated by reference) is carried out. Four to thirty female mice, aged approximately 8–10 weeks, are ovariectomized. Administration of a compound of the invention is begun within three weeks after castration on the experimental group. After one week of administration of a compound of formula 1, the mice are immunized with rat type II collagen. The mice are graded for clinical severity of arthritis, as set out in Holmdahl et al., Arthritis Rheum., 29, 106 (1986), herein incorporated by reference. Sera are collected, and assayed for anti-type II collagen reactive antibodies. At the termination of the experiment, spleen cells are obtained from the mice for determination of T cell activity.

Activity Is illustrated by a reduction in titer of anti-collagen type II antibodies determined by conventional ELISA assay. Reduction in T-cell reactivity to type II collagen presented to splenic T-cells by antigen presenting cells is evaluated by quantitation of DNA synthesis by thymidine uptake. Finally, clinical severity of disease is evaluated daily by defining first signs of erythema and swelling of one or more limbs. Clinical assessment is correlated with histologic examination.

Assay 1

Between four and thirty young adult female Sprague-Dawley rats are fed animal chow and water ad libitum. The experimental group receives a compound of formula 1, and all rats receive rat cord generally as described in Amason et al., Arch. Neurol., 21, 103–108 (1969), incorporated herein by reference. The rats are graded for signs of experimental allergic encephalomyelitis (EAE). Between three and seven weeks after administration of a compound formula 1 began, the rats are sacrificed, their spinal cords removed and examined.

Activity is illustrated by the ability of a compound to inhibit EAE.

Assay 3

Between five and fifty mice (MRL/Ipr and NZB) are used. Reduction of anti-DNA antibodies, quantitated by ELISA, as well as changes in survival time and histologic exam of kidneys are evaluated parameters. The mice are dosed with compounds of the invention and are evaluated using the above parameters for disease progression.

Assay 4

Five to fifty women are selected for the clinical study. The women are post-menopausal, i.e., have cased menstruating for between 6 and 12 months prior to the study's initiation, suffer from an autoimmune disease which exhibits symptoms, but otherwise are in good general health. Because of the idiosyncratic and subjective nature of these disorders, the study has a placebo-control group, i.e., the women are divided into two groups, one of which receives a compound of formula 1 as the active agent and the other receives a placebo. Women in the test group receive between 50–200 mg of the drug per day by the oral route. They continue this therapy for 3–12 months. Accurate records are kept as to the number and severity of the symptoms in both groups and at the end of the study these results are compared. The results are compared both between members of each group and also the results for each patient are compared to the symptoms reported by each patient before the study began.

Utility of the compounds of formula I is illustrated by the positive impact they have in at least one of the assays described above.

ASSAY FOR PROTECTION OF ISCHEMIC MYOCARDIUM AGAINST REPERFUSION DAMAGE

Ten male and ten female rabbits are treated with 1 mg of a compound of formula I. After 15 minutes, the rabbits are anesthetized and the coronary arteries are occluded for 30 minutes followed by four hours of reperfusion.

Comparable control groups are treated with vehicle.

The risk zone is assessed by blue dye and the infarct zone tetrazolium staining. A reduced size of infarct zone relative to the control shows that the compound of formula I is effective in inhibiting reperfusion damage to ischemic myocardium.

Test Method To Show Increased Testosterone

Sixty generally healthy men between the ages of 62 to 75 are selected for evaluation based on the following criteria:

Inclusions

1. Body weight between 90 and 130% of the mid-range of ideal body weight as defined by the Metropolitan Life Insurance Table (Appendix 1) for men of average frame.

2. Serum testosterone at screening less than 500 ng/dl.

3. Serum prostate specific antigen for less than or equal to 4 ng/ml.

4. Normal clinical prostate exam and the absence of suspicious nodules on screening prostate ultrasound.

5. No significant act of medical illnesses such as angina, myocardial infarction or angioplasty within the past 2 years, history of visceral cancer within the previous 5 years or prostate cancer at any time.

6. Normal physical examination at screening, including normal cardiopulmonary exam, absence of peripheral vascular or venus disease, or other evidence of systemic disease.

7. The following must be within 10% of the upper or lower range limits of normal as reported by the reference laboratory: CBC, including hemoglobin, hematocrit and total WBC.

Exclusions

1. Men who smoke.

2. Men with a previous history of thromboembolic disease or pulmonary embolus at any time in the past.

3. Men who consume more than 2 units of alcohol per day, equivalent to approximately 2 glasses of wine, 2 bottles of beer.

4. Clinically significant abnormalities on screening electrocardiogram.

The study is of parallel design and placebo controlled comparing two doses of a compound of formula I at 10 and 40 mg/day vs. placebo for 14 weeks. Subjects are randomized to compound or placebo. Testosterone levels are measured every two weeks with the RIA, Coat-a-Count Kit available from Diagnostic Products Co. 5700 W. 96th Street, Los Angeles, Calif. 90045. A statistically significant increase in testosterone levels over the placebo indicates that a compound of formula I is effective in increasing serum testosterone.

We claim:

1. A method of inhibiting a pathological condition wherein said pathological condition is Alzheimer's disease which comprises administering to a mammal in need of said pathological condition an effective amount of (−)-Cis-6-phenyl-5-[4-(2-pyrrolidin- 1-yl-ethoxy)-phenyl]-5,6,7,8-tetrahydronaphthalen-2-ol.

* * * * *